T 864008

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED JULY 15, 1969

864 O.G. 730

784,946

REACTIVATION OF OXIDE CATALYSTS

Warren E. Campbell, P.O. Box 511,
Kingsport, Tenn. 37662

Filed Dec. 18, 1968. Published July 15, 1969
Int. Cl. B01j *11/66;* C07c *51/16, 121/02*
U.S. Cl. 252—411
No Drawing. 6 Pages Specification

Catalytic activity of a metal-oxide catalyst, which has been deactivated by excessive heat treatment in the presence of an oxygen-containing gas, can be restored by heating the deactivated catalyst at high temperature with a reducing gas or gaseous mixture. More specifically the reactivation or preconditioning is directed to oxidation and ammoxidation catalysts used in the preparation of acids, anhydrides and nitriles from hydrocarbons such as propylene and p-xylene. In particular the treated catalysts contain the oxides of niobium and molybdenum or the oxides of arsenic, niobium and molybdenum. The catalysts may be supported on silica. It is also expected that the above compositions in which tantalum is used to replace niobium may be reactivated. The catalytic metals exist in an oxidation state above zero. Molybdenum may be present in the form of a heteropolyacid such as ceri-12-molybdic acid. The gas used for the catalyst reduction may be any easily oxidizable material. For example, olefins and long chain n-hydrocarbons may be used. Propylene is the preferred reducing gas. Ammonia or hydrogen may also be employed as a reducing gas. The reduction treatment is carried out at temperatures between 350° C. and 650° C. The catalyst may additionally be treated with $As_2O_3$.